United States Patent [19]
Santoro

[11] Patent Number: 5,217,031
[45] Date of Patent: Jun. 8, 1993

[54] MOTOR-DRIVEN APPARATUS FOR CLEANING SPACES BETWEEN TEETH BY DENTAL FLOSS

[76] Inventor: Giovanni Santoro, Via Campodimele, 55-00189 Roma, Italy

[21] Appl. No.: 761,929

[22] PCT Filed: Mar. 20, 1990

[86] PCT No.: PCT/IT90/00031
§ 371 Date: Sep. 17, 1991
§ 102(e) Date: Sep. 17, 1991

[87] PCT Pub. No.: WO90/11057
PCT Pub. Date: Oct. 4, 1990

[30] Foreign Application Priority Data
Mar. 21, 1989 [IT] Italy .................. 47764 A/89

[51] Int. Cl.$^5$ ............................. A61C 15/00
[52] U.S. Cl. ................................. 132/322
[58] Field of Search ............. 132/321, 322, 323, 324, 132/325, 326, 329

[56] References Cited

U.S. PATENT DOCUMENTS

| | | | |
|---|---|---|---|
| 3,667,483 | 6/1972 | McCabe | 132/322 |
| 3,756,274 | 9/1973 | Warner | 132/325 |
| 3,847,167 | 11/1974 | Brien | 132/92 |
| 4,245,658 | 1/1981 | Lecouturier | 132/92 |
| 4,586,521 | 5/1986 | Urso | 132/92 |
| 4,706,695 | 11/1987 | Urso | 132/92 |

Primary Examiner—Cary E. O'Connor
Attorney, Agent, or Firm—DeLio & Peterson

[57] ABSTRACT

Motor-driven apparatus for cleaning spaces between teeth by dental floss comprising a dental floss for cleaning the spaces between teeth, motor means (11), a feeding reel (24) of the fresh dental floss, a take-up reel (25) of the worn-out dental floss, a set of pulleys (18, 20, 21A, 21B) about which the dental floss is running between feeding reel and take-up reel, and reciprocating motor means (13, 15, 16, 18) to reciprocate the operating length of the dental floss as well as to keep it stretched and to replace the dental floss as it is worn-out.

7 Claims, 1 Drawing Sheet

MOTOR-DRIVEN APPARATUS FOR CLEANING SPACES BETWEEN TEETH BY DENTAL FLOSS

This invention relates to a motor-driven apparatus for cleaning spaces between teeth by dental floss comprising a dental floss for cleaning the spaces between teeth, motor means, a feeding reel of the fresh dental floss, a take-up reel of the worn-out dental floss, a set of pulleys about which the dental floss is running between feeding reel and take-up reel, and reciprocating motor means to reciprocate the operating length of the dental floss as well as to keep it stretched and to replace the dental floss as it is worn out.

As known, in order to prevent tooth decays and swollen gums it is very important to keep the spaces between teeth strictly clean.

At present there are commercially available dental flosses satisfactorily performing their cleaning function by the introduction into each space between adjacent teeth and the reciprocation caused by pulling and releasing the dental floss stretched between the left hand and the right hand of the user.

There are also available fork frames to be used by hand and having prongs between which a floss is stretched and moved like a reciprocating saw.

Such fixtures besides being efficient only when used by care and patience are not suitable for a rational use of the dental floss, some lengths of which are not conveniently exploited.

On the other hand, in the field of tooth and gum cleaning the problems of an irrational use of the toothbrush have been almost solved by the commercially available motor-driven tooth-brushes. Therefore the applicant has sought to provide a motor-driven apparatus for the rational use of the dental floss for cleaning the spaces between teeth.

To this end the applicant has devised an apparatus comprising a small-size casing to be introduced into the mouth and in which a length of dental floss is exposed to the outside through an opening, and means able both to reciprocate such a length of dental floss and to feed it step by step so that it can be replaced by fresh floss as it is worn-out.

In this field document U.S. Pat. No. 4,245,658 discloses an automatic flossing apparatus which stores the dental floss, holds it automatically under tension and agitates and renews the floss during its manipulations. The floss unwinds from one spool and rolls on another automatically. The floss makes a complete circuit passing by an oscillator imparting back and forth movements to the floss and subsequently to a two-pronged headpiece holding the floss under tension across the two prongs. The spools are connected by a clutch and crank transmission mechanism which maintains controllable floss tension.

The construction of the apparatus is extremely complicated and requires a very large number of component parts cooperating together to perform its function.

The oscillating action is caused by the motor, the shaft of which is oscillating due to the utilization of a cam. The circuit followed by the dental floss is very long and involves a great deal of bends around an equal number of guide members with the danger of tangling. Furthermore the spools are connected by a complicated transmission mechanism comprising a crank, a belt, biassing and subtension springs and pressure wheels.

As it will be self evident this construction, besides being very complicated and consequently expensive, seems to be likely to raise operation problems.

The present invention will be now described into detail with reference to the annexed drawing, in which.

Figure 1:
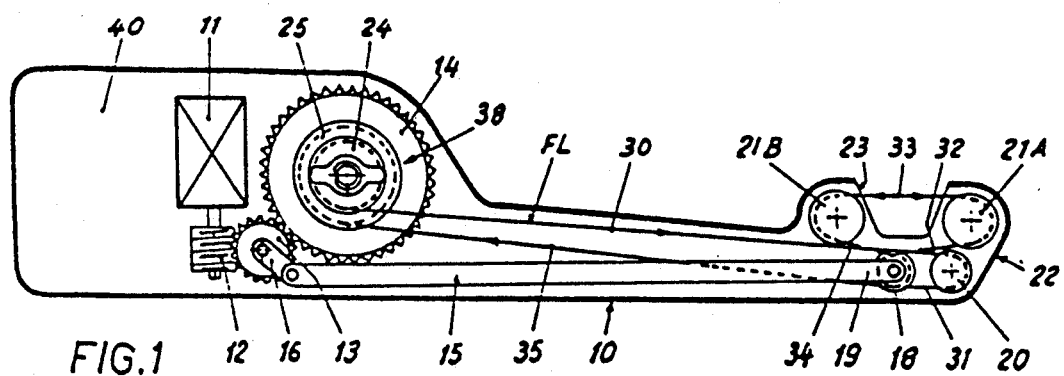
FIG. 1 is a somewhat schematic view of an embodiment of the apparatus in longitudinal section to show the internal mechanism in one position of the reciprocated connecting rod.
Figure 2:
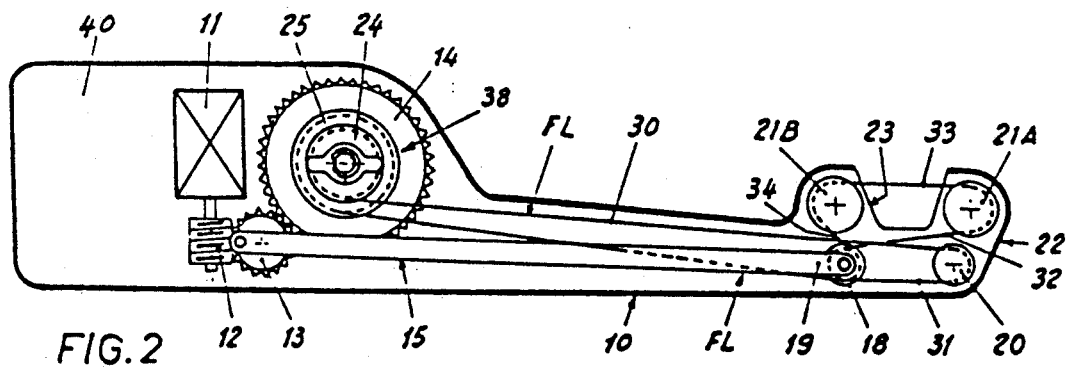
FIG. 2 is a similar view of the apparatus with the connecting rod in a different position.

With reference firstly to FIGS. 1 and 2 the apparatus according to the invention comprises a casing 10; a motor 11 provided with reduction gear and helical driving gear 12; a first gear wheel 13 of small diameter meshed with gear 12 and idle-mounted on casing 10; a second gear wheel 14 of greater diameter also idle-mounted in casing 10 and meshed with the first gear wheel 13; a connecting rod 15 driven by the first gear wheel 13 by means of a crank 16 integral with the latter; a first pulley 18 mounted at the end 19 of the connecting rod 15; a second pulley 20 idle-mounted in casing 10 and facing pulley 18, and a pair of free pulleys 21A, 21B idle-mounted in the head 22 of casing 10 at both sides of opening 23.

Figure 3:
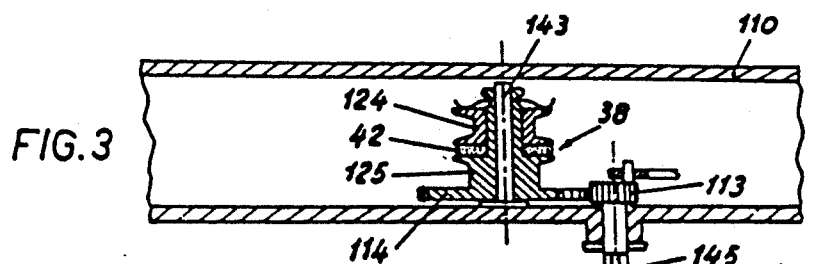
FIG. 3 is a fragmentary section in enlarged scale showing another embodiment with handle and casing separated from each other and a feasible cluth device.

The apparatus further includes a feeding reel 24 of the fresh dental floss and a take-up reel 25 of the worn-out dental floss. It should be noted that the take-up reel is integral with the second gear wheel 14, while the feeding reel in this embodiment is coaxially mounted with the assembly formed of the second gear wheel and the take-up reel with the interposition of a clutch device, as shown in the embodiment of FIG. 3.

Figure 4:
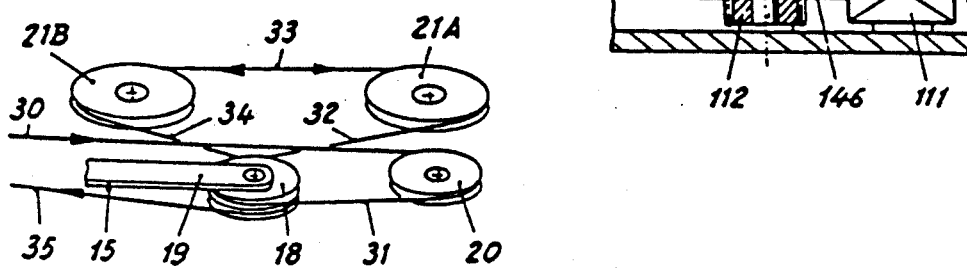
FIG. 4 is a detailed view of the pulleys stretching the dental floss and the reciprocated double pulley.

For a fully understanding of the description, floss FL, cleaning the spaces between teeth and extending from feeding reel 24 to take-up reel 25 around several pulleys as described herebelow in greater detail, is divided in several lengths, each of them extending from a pulley to the next one. Therefore the first length between feeding reel 24 and pulley 20 is designated by 30; the second length between pulley 20 and double pulley 18 is designated by 31; the third length between pulley 18 and pulley 21A is indicated at 32; the length between pulley 21A and pulley 21B is indicated at 33, the latter being the operating length; the length between pulley 21B and pulley 18 is indicated at 34; and finally the length between pulley 18 and take-up reel 25 is designated by 35 (FIG. 4).

As known the active length of the dental floss for cleaning spaces between teeth should be reciprocated in the apparatus of this invention due to the rotation of pulley 18 mounted at the end 19 of the connecting rod 15.

To this end the clutch device mounted between feeding reel 24 and its support member is mandatory.

In operation, motor 11 rotates gear wheel 13 which reciprocates through crank 16 the double pulley 18 approaching and moving away from pulley 20, as shown in FIGS. 1 and 2.

Since length 30 of dental floss FL is held by clutch device 38 (FIG. 3) this relative movement of double pulley 18 causes length 33 stretched between the freely rotating pulleys 21A and 21B, to run with respect to window 23. It should be appreciated that the pulleys are arranged such that length 33 is shifted in both direction by a double as high extent than that of the reciprocated pulley 18 due to the so called chain pulley effect (FIG. 4).

As for the details of this movement it should be noted that the reciprocation of central floss length 33 is caused by the alternate variation of the length of the floss loops formed of lengths 30, 31 and lengths 34, 35, respectively.

It should also be appreciated that the rotation of gear wheel 13 causes also gear wheel 14 to be rotated even if much more slowly due to the tooth ratio of the gear wheels.

The rotation of gear wheel 14 likewise causes take-up reel 25 to be rotated (FIG. 3), thus pulling the dental floss in one direction by a greater force than that of the clutch device 38 in the opposite direction, so that dental floss FL is unwound a little at time from feeding reel 24. Thus the dental floss of the operating length 33 is continuously replaced by fresh floss, the worn-out floss being wound on take-up reel 25.

The movement of the floss from feeding reel 24 to take-up reel 25 is designated by arrows along the path of the dental floss indicating also the reciprocation of the operating length 33 and the adjacent lengths.

In the embodiment of FIGS. 1 and 2 the motor and the housing of the cells (not shown) are located in the handle 40 of the casing 10.

In FIG. 3 a second embodiment is shown in fragmentary exploded section, in which casing 110 and handle 140 are separated and adapted to be fitted by snap means of known type (not shown). In FIG. 3 a clutch device 38, adapted to be included also in the embodiment of FIGS. 1 and 2, is also shown in detail.

Clutch device 38 is provided with friction felt 42 placed between the one-piece assembly of gear wheel 114/take-up reel 125 and feeding reel 124 coaxially mounted on pin 143.

Handle 141 and casing 110, the latter being of disposable type and being replaced when all of the dental floss is passed from feeding reel 124 to take-up reel 125, are connected by snap means of known type which are not further described. However, the coaxial arrangement of the two reels 24 (or 124) and 25 (or 125) with the gear wheel of larger diameter 14 (or 114) should be appreciated.

Of course, in the embodiment of FIG. 3 some parts have a different construction from the embodiment of FIGS. 1 and 2, even if they have the same function of transmitting the movement of motor 111 to gear wheel 113 carrying crank 16; among them there is in particular the coupling of key pin 145 of the latter into the cavity of gear 112 driven by motor shaft 146.

I claim:

1. Motor-driven apparatus for cleaning spaces between teeth by dental floss (FL) comprising an outer casing (10) provided with handle (40), a dental floss (FL) for cleaning the spaces between teeth, an electrical motor (11), a feeding reel (24) of the fresh dental floss, a take-up reel (25) of the worn-out dental floss, a set of stationary pulleys (20, 21A, 21B) around which the dental floss is running between the feeding reel (24) and the take-up reel (25), and reciprocating drive means (13, 15, 16) to reciprocate the operating length (33) of the dental floss (FL) as well as to keep it stretched and to replace the dental floss as it is worn-out characterized in that said electrical motor continuously rotating, drives reciprocating driving means (13, 15, 16, 18) for reciprocating said operating length (33) of the dental floss, comprising a first gear wheel of small diameter (13) mounted on said casing (10) and meshing with a gear (12) mounted on a shaft of said electrical motor (11); a crank (16) operated by said small gear wheel (13), a second gear wheel (14) of larger diameter, mounted on said casing (10) and meshed with said first gear (13), a rod (15) linked at one end to said crank (16), and a double pulley (18) mounted on the free end (19) of said rod and reciprocating therewith.

2. The motor driven apparatus for cleaning the spaces between teeth of claim 1, wherein said set of stationary pulleys comprises a first pulley (20) mounted on said outer casing (10) facing said reciprocating double pulley (18) and a pair of identical pulleys (21A, 21B) mounted on the sides of an opening (23) formed on the head (22) of said outer casing (10) between which pulleys (21A, 21B) said operating length (33) of the dental floss (FL) is stretched.

3. The motor-driven apparatus for cleaning the spaces between teeth of claim 2, wherein said second gear wheel (14) and said take-up reel (25) are integral with each other, thus forming an unitary assembly (14, 25) and said feeding reel (24) is mounted on the axis of said unitary assembly and concentrically therewith with the interposition of a clutch device (38).

4. The motor-driven apparatus for cleaning the spaces between teeth of claim 3, wherein the reciprocating movement of said operating length (33) of dental floss is due to the alternate variation of the length of a first loop of dental floss comprising the length (30, 31) of floss comprised between the feeding reel (24) and the double pulley (18) and passing around said first stationary pulley (20), and a second loop of dental floss comprising the length (34, 35) of floss comprised between one (21B) of said pair of stationary pulleys and said take-up reel (25) and passing around said double pulley (18).

5. The motor-driven apparatus for cleaning the spaces between teeth of claim 4, wherein rotation of said small gear wheel (13) causes said larger gear wheel (14) also to rotate together with said take-up reel (25) that, accordingly, pulls dental floss (FL) in one direction with a greater force than the force opposed by said feeding reel (24) owing to the differential rotating movement thereof allowed by said clutch device interposed between said feeding reel (24) and said take-up reel (25) concentrically mounted.

6. The motor-driven apparatus for cleaning the spaces between teeth of claim 5, wherein said clutch device (38) comprises a disc of a friction felt (42) having the same diameter of said feeding reel (24).

7. The motor-driven apparatus for cleaning the spaces between teeth of claim 5, wherein said casing (110) and said handle (140) are separable, said casing (110) being of the disposable type and said handle (140) includes said electrical motor (111) and relative cells.

* * * * *

UNITED STATES PATENT AND TRADEMARK OFFICE
CERTIFICATE OF CORRECTION

PATENT NO. : 5,217,031

DATED : June 8, 1993

INVENTOR(S) : Giovanni SANTORO

It is certified that error appears in the above-identified patent and that said Letters Patent is hereby corrected as shown below:

<u>TITLE PAGE, IN THE ABSTRACT</u>

In line 2, delete "by" and substitute therefor -- with --.

In line 2, delete "a dental floss for clean-".

In line 3, delete "ing the spaces between teeth", and substitute therefor -- an electric --.

In line 4, delete "of the" and substitute therefor -- for --.

In line 5, before "the", delete "of" and substitute therefor -- for --.

In line 6, delete "is running" and substitute therefor -- runs --.

In line 7, before "feeding", insert -- the --.

In line 7, before "take-up", insert -- the --.

In line 7, before "reciprocating", insert -- a --.

In line 8, delete "motor means" and substitute therefor -- drive --.

Signed and Sealed this

Eighth Day of March, 1994

Attest:

BRUCE LEHMAN

Attesting Officer

Commissioner of Patents and Trademarks